(12) United States Patent
Schimitzek

(10) Patent No.: US 9,786,060 B2
(45) Date of Patent: Oct. 10, 2017

(54) DEVICE FOR CONTROLLING THE ANESTHETIZATION OF AN ANIMAL TO BE SLAUGHTERED

(71) Applicant: CSB-SYSTEM AG, Geilenkirchen (DE)

(72) Inventor: Peter Schimitzek, Geilenkirchen (DE)

(73) Assignee: CSB-System AG, Geilenkirchen (DE)

( * ) Notice: Subject to any disclaimer, the term of this patent is extended or adjusted under 35 U.S.C. 154(b) by 0 days.

(21) Appl. No.: 15/503,457

(22) PCT Filed: Aug. 11, 2015

(86) PCT No.: PCT/DE2015/000398
§ 371 (c)(1),
(2) Date: Feb. 13, 2017

(87) PCT Pub. No.: WO2016/023534
PCT Pub. Date: Feb. 18, 2016

(65) Prior Publication Data
US 2017/0249747 A1 Aug. 31, 2017

(30) Foreign Application Priority Data
Aug. 13, 2014 (DE) .................. 20 2014 006 472 U

(51) Int. Cl.
*A22B 3/00* (2006.01)
*G06T 7/20* (2017.01)
(Continued)

(52) U.S. Cl.
CPC .................. *G06T 7/20* (2013.01); *A61D 7/04* (2013.01); *G01S 17/89* (2013.01); *A22B 3/00* (2013.01);
(Continued)

(58) Field of Classification Search
CPC .. A22B 3/00; A22B 3/06; A22B 3/086; A22B 3/10; A22B 5/00; A61D 7/00;
(Continued)

(56) References Cited

U.S. PATENT DOCUMENTS

| 5,186,677 A * | 2/1993 | Christensen ............. A22B 1/00 452/53 |
| 6,899,613 B2 * | 5/2005 | van den Nieuwelaar ............ A22B 3/005 452/63 |

(Continued)

FOREIGN PATENT DOCUMENTS

DE 102011077944 A1 12/2012
DE 202013002484 U1 7/2014
(Continued)

*Primary Examiner* — Richard Price, Jr.
(74) *Attorney, Agent, or Firm* — Laurence A. Greenberg; Werner H. Stemer; Ralph E. Locher

(57) ABSTRACT

A device for controlling the anesthetization of an animal to be slaughtered. The device includes a stimulation unit via which a stimulation stimulus is given to the animal. The device includes an image capturing unit that has an image capturing range. The image capturing unit is constructed as a 3D-camera. One part of a surface of the animal is optically detected in the image capturing range and range pixels are collected in the area of the surface. The range pixels are provided and transmitted as pixel data. An evaluation unit is connected to the image capturing unit and collects the pixel data provided by the image capturing unit. The evaluation unit determines an active movement of the animal from the detected pixel data and provides and transmits the control result in the event of a determined movement of the animal.

7 Claims, 1 Drawing Sheet

(51) Int. Cl.
   *G01S 17/89* (2006.01)
   *A61D 7/04* (2006.01)
   A61B 5/00 (2006.01)
   A61B 5/11 (2006.01)
(52) U.S. Cl.
   CPC .......... *A61B 5/0077* (2013.01); *A61B 5/1128* (2013.01); *G06T 2207/10028* (2013.01)
(58) Field of Classification Search
   CPC .......... A61D 7/04; G06T 7/00; G06T 7/0002; G06T 7/20; G06T 7/0007; G06T 7/215
   USPC ............................. 452/52, 57, 58, 63, 66, 67
   See application file for complete search history.

(56) References Cited

U.S. PATENT DOCUMENTS

| | | | |
|---|---|---|---|
| 7,448,943 B1* | 11/2008 | Woodford | A22B 3/005 452/66 |
| 7,662,030 B2* | 2/2010 | Cheek | A22B 3/086 452/57 |
| 8,113,926 B1* | 2/2012 | Cheek | A22B 3/00 452/66 |
| 2016/0029648 A1 | 2/2016 | Schmitzek | |

FOREIGN PATENT DOCUMENTS

| | | |
|---|---|---|
| EP | 2389809 A2 | 11/2011 |
| WO | 2013052001 A1 | 4/2013 |
| WO | 2014037015 A1 | 3/2014 |

\* cited by examiner

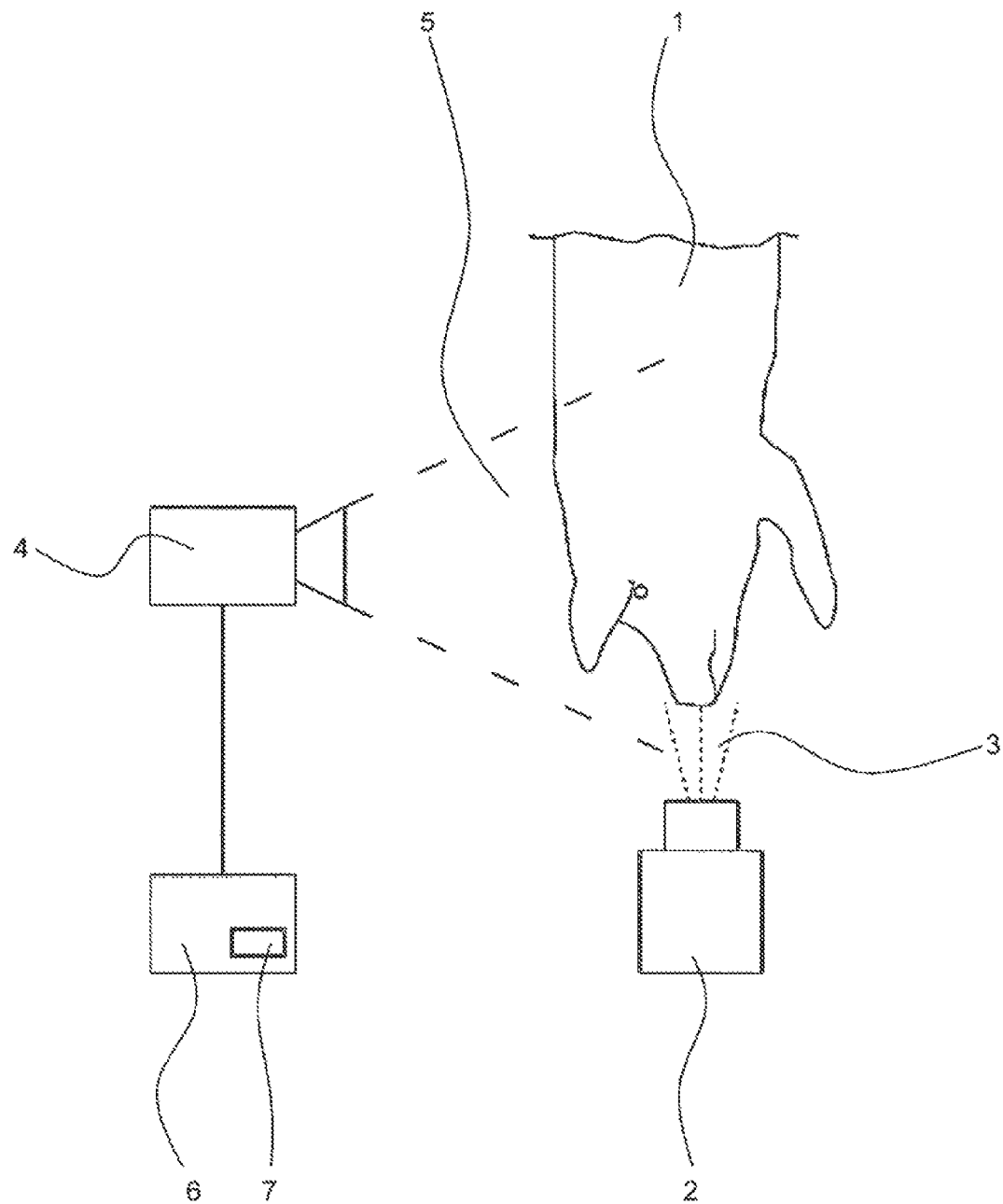

DEVICE FOR CONTROLLING THE ANESTHETIZATION OF AN ANIMAL TO BE SLAUGHTERED

BACKGROUND OF THE INVENTION

Field of the Invention

The invention relates to an apparatus for checking the stunning of an animal for slaughter within processing of animals for slaughter.

During processing of animals for slaughter, it is normally prescribed for the animals for slaughter to be stunned before the actual slaughter process. Depending on the type of animal for slaughter, stunning is effected in this case by shooting a bolt, electric stunning or by means of $CO_2$ stunning. Stunning is used particularly to prevent unnecessary suffering for the animal during slaughter.

In this context, the present invention is based on the problem of the stunning performed for the animal for slaughter sometimes possibly failing or lasting only an inadequately long time, which means that the animal for slaughter possibly regains consciousness, particularly during exsanguination. To prevent this, it is now prescribed in the European Union that a stun check is performed in abattoirs. Such a stun check provides for a monitoring method and regular checks on stun quality, inter alia.

From the prior art, it is known that a stun check of this kind is performed by appropriately trained personnel who monitor the respective animal for slaughter after stunning and during exsanguination for any reactions or symptoms that may occur.

If the monitoring reveals that stunning was unsuccessful, the animal for slaughter is restunned.

Such monitoring of the stunning is very personnel intensive, however, and accordingly expensive to perform.

In addition, subjective assessment of stun quality can also give rise to misinterpretations by the relevant personnel.

BRIEF SUMMARY OF THE INVENTION

The object of the present invention is to provide an apparatus for checking the stunning of an animal for slaughter that allows a reliable, fast and inexpensive check on the stunning of an animal for slaughter within processing of animals for slaughter.

The object is achieved by an apparatus having the features presented in independent claims. Preferred developments arise from the dependent claims.

An apparatus according to the invention for checking the stunning of an animal for slaughter is provided downstream of a stunning station within processing of animals for slaughter, so that a check on stunning, particularly before the exsanguination process or before scalding, is performable.

The apparatus is in this case involved in the process of processing animals for slaughter such that the animal for slaughter that is to be checked, on the path of its transport, preferably along a conventional tubular track, passes through the region of action of the apparatus.

The apparatus firstly has, according to the invention, a stimulation unit that can be used to deliver a stimulation stimulus to the animal for slaughter.

A stimulation stimulus is understood in the present context to mean a stimulus to which the animal for slaughter would react with appropriate physical reactions, for example a twitching movement, if stunning were inadequate.

Furthermore, the apparatus according to the invention has an image capture unit having an image capture region, wherein the image capture unit, according to the invention, is in the form of a 3D camera.

The 3D camera in this case provides the particular advantage that firstly particularly the active movement of the animal for slaughter is detectable particularly finely, that is to say in the millimeter range, and that additionally movement detection is performable even without stipulated reference points.

Secondly, a 3D camera can also be used to detect active movements of the animal for slaughter parallel to the optical axis of the 3D camera, that is to say movements toward the camera or away from the camera.

Further advantages of the 3D camera are additionally that 3D cameras can provide metrically calibrated data, such as the coordinates of an image point, as x, y and z values in a Euclidean coordinate system within the image itself. This facilitates the distinction between active movements and transport-dependent passive movements in the evaluation.

A further advantage is provided by the circumstance that, depending on design, they may have an integrated pattern projector, which means that it is then possible to dispense with an external light source for illuminating the animal for slaughter. In this way, it is firstly possible to keep down the costs of providing an apparatus according to the invention for checking on stunning. Secondly, dispensing with an external light source allows the apparatus to be produced in correspondingly small form. Similarly, in the case of the present form of the invention, it is possible, as a further advantage, to dispense with a background plate that is generally intended to facilitate optical detection of the animal for slaughter as a whole and to protect employees against possible dazzling by illumination.

In a preferred development, two image capture units having a respective associated image capture region may be arranged and connected to the evaluation unit, the optical axes of the two image capture units being arranged at an angle, for example at right angles, to one another in order to be able to detect active movements of the animal for slaughter particularly reliably.

A section of a surface of the animal for slaughter is optically capturable in the image capture region, discrete image points, with their spatial coordinates and preferably a brightness or color value, being capturable in the section of the surface.

The captured image points are subsequently provided by the image capture unit in a manner transmittable as image point data.

As a further component, the apparatus according to the invention has an evaluation unit.

The evaluation unit is connected to the image capture unit and capable firstly of capturing the image point data provided by the image capture unit and secondly of ascertaining an active movement of the animal for slaughter from the captured image point data.

An active movement is understood in the present case to mean a proper movement by the animal for slaughter that is caused by muscle contractions as a result of the stimulation stimulus and that is deemed to be a safe indication that the stunning performed previously is inadequate.

The active movement differs in this case significantly from the regular, horizontal passive movement that the animal for slaughter makes on account of its transport along the roller track.

The section on the surface of the animal for slaughter that is captured in the image capture region of the image capture unit is in this case located in a previously stipulated region in which the active movement to be expected from the animal for slaughter turns out to be greatest.

If the evaluation unit ascertains an active movement of the animal for slaughter, then a check result providing the information that the stunning of the animal for slaughter is inadequate is immediately provided in outputtable form.

Both the capture of the image point data and the ascertainment of any active movement and provision of the check result are effected in real time according to the invention, so that inadequate stunning of the animal for slaughter is establishable in good time before the subsequent processing steps, particularly exsanguination or scalding, and the animal for slaughter can immediately be restunned.

The solution according to the invention is not restricted in this case to the provision of the check result when an active movement is established. Rather, the evaluation unit is likewise capable of outputting an appropriate check result when an active movement is not established, which check result then states that the stunning of the animal for slaughter has been performed correctly and is effective.

The apparatus according to the invention particularly has the advantage that, in line with current and future animal protection regulations, a safe check on the stunning of the respective animal for slaughter is providable in real time within the process of processing the animal for slaughter. Further, there is the advantage that the stun check is performed in objectified fashion and errors as a result of abstractions or misinterpretations, as can arise in the case of a visual check by personnel, are avoided. Additionally, there is the advantage that the check is performable in manipulation-proof fashion and the check result is documentable and storable and hence archivable. The check result is in this case preferably associated with the identification of the animal for slaughter. Advantageously, the evaluation unit is connected to a central control unit and a central database of the abattoir. In addition, as a further advantage, it is possible to very largely dispense with the use of personnel at this point in the process of processing animals for slaughter, which particularly lowers the costs for the stun check and hence for the overall process of processing animals for slaughter.

In a development of the invention, the evaluation unit is additionally connected to the stimulation unit and capable of controlling delivery of the stimulation stimulus.

In this case, preferably the evaluation unit can take captured image point data as a basis for ascertaining the correct positioning of the animal for slaughter with respect to the stimulation unit and, when a stipulated final position of the animal for slaughter is reached, can send an appropriate signal for delivering the stimulation stimulus to the stimulation unit. As a particular advantage, this development can also involve delivery of the stimulation stimulus being associated with the check result and also documented and archived.

A preferred development of the invention additionally provides for the 3D camera to be in the form of a TOF camera (time of flight camera).

A TOF camera of this kind allows ascertainment of a distance between it and a captured object by means of the time of flight method.

In this case, the TOF camera particularly has the advantages that TOF cameras normally have a simple design and hence can be provided inexpensively and that they can realize high frame rates by virtue of the entire object, in the present case the animal for slaughter or a relevant region of the animal for slaughter, being mappable in a photograph in a very short time.

Further, the coordinates of an image point can be obtained as x, y and z values, that is to say the spatial coordinate data, without further image evaluation, so that the spatial coordinate data of optically regular surfaces can also immediately be obtained and evaluated without the need to use a projection pattern, for example.

In a particularly advantageous development of the invention, the stimulation unit can be used to deliver a contactless stimulation stimulus to the animal for slaughter.

Delivery of a contactless stimulation stimulus to the animal for slaughter particularly provides the advantage that this can effectively prevent contamination of the animal for slaughter by any elements of the stimulation apparatus that transmit the stimulation stimulus.

In a further advantageous variant of the invention, the stimulation unit can deliver a thermal stimulation stimulus to the animal for slaughter.

The advantages of a thermal stimulation stimulus are in this case primarily the simple and technically uncomplicated provision and the freely selectable distance between stimulation unit and animal for slaughter, on the basis of the temperature of the stimulation stimulus.

The thermal stimulation stimulus can be provided in the present case by a jet of hot water, for example.

In a preferred development, the thermal stimulation stimulus is a jet of steam, which, as a particular advantage, can be delivered very specifically to sensitive regions of the animal for slaughter, for example the nose region.

An advantageous form of the apparatus according to the invention provides for the check result to be able to be used to control external units.

In this context, external units are, by way of example, sorting units that, when an active movement of the animal for slaughter is ascertained by the evaluation unit, perform outward transfer of the animal for slaughter from the ongoing process of processing animals for slaughter and route said animal to manual or automatic restunning.

Furthermore, external units may be restunning units in the present case, which are integrated into the process of processing animals for slaughter following the stun check and which take the check result as a basis for performing restunning of the animal for slaughter if necessary.

In the form presented here, the check result is preferably provided in a form outputtable as a control signal that is capturable and processable by the external units.

The advantage of the present form of the invention is particularly that when an active movement of the animal for slaughter is ascertained, said animal can be routed to restunning in the shortest time and hence unnecessary suffering for the animal for slaughter can be prevented as quickly as possible. In addition, in this way, the process of processing animals for slaughter is impaired only insubstantially.

After restunning has been performed, the animal for slaughter is preferably routed afresh to the apparatus for checking on stunning, in which a fresh check on the effectiveness of the stunning is then carried out.

The check result provided by the evaluation unit is, in a preferred development of the invention, associable with a data record relating to an animal for slaughter.

Such a data record is preferably already stored in the evaluation unit and has particularly an identification code for an animal for slaughter, and details regarding the type of animal for slaughter and regarding the dimensions thereof, and also regarding the place of origin thereof.

As a particular advantage, the association of the check result with the data record relating to an animal for slaughter allows the performed stun check to be archived in accordance with the respective animal for slaughter and hence detailed evidence to be produced for whether, particularly from the point of view of animal protection law, the stunning of the animal for slaughter was performed correctly and was effective during processing of the animal for slaughter.

BRIEF DESCRIPTION OF THE VIEW OF THE DRAWING

The invention is explained in more detail as an exemplary embodiment with reference to the FIGURE of the drawing, a basic depiction in a view from the side.

DESCRIPTION OF THE INVENTION

The FIGURE shows the apparatus according to the invention for checking the stunning of an animal for slaughter 1 as a basic depiction in a view from the side, only the relevant region of the animal for slaughter 1 being depicted for the sake of clarity. The animal for slaughter 1 is a pig for slaughter in the present case.

The apparatus according to the invention is provided downstream of a stunning station (not depicted) and particularly upstream of an exsanguination station (not depicted) or upstream of a scalding station (not depicted) within processing of animals for slaughter.

As depicted in the FIGURE, the apparatus has a stimulation unit 2 that can be used to deliver a stimulation stimulus 3 to the animal for slaughter 1. In the present case, the apparatus according to the invention is arranged within the processing of animals for slaughter such that the animal for slaughter 1 is moved over the stimulation unit 2 in a manner suspended head first, for example by guidance on a roller track (not depicted).

In the present exemplary embodiment, the stimulation stimulus 3 is in the form of a hot jet of steam that acts particularly on the sensitive nose region of the animal for slaughter 1.

Provision of the stimulation stimulus 3 is based on the consideration that the animal for slaughter 1 would, given inadequate stunning, give a physical reaction to the stimulation stimulus 3.

The apparatus according to the invention further has an image capture unit 4, in the present case in the form of a color value camera, having an image capture region 5.

The image capture unit 4 is in this case oriented with respect to the animal for slaughter 1 such that a relevant section of the surface of the animal for slaughter 1 is capturable in the image capture region 5, in which section an active movement of the animal for slaughter 1 can be expected in the event of a reaction to the stimulation stimulus 3 as a result of deficient stunning.

The stipulation of the correspondingly relevant section of the surface of the animal for slaughter 1 is performed on the basis of empirical examinations, for example. A relevant section may also be the entire animal for slaughter, for example from a side perspective.

The relevant section of the surface is capturable in the image capture region 5 on the basis of discrete image points, the image points being capturable by the image capture unit 4, for example with the surface area coordinates thereof and a color value.

The captured image points are subsequently provided by the image capture unit 4 in real time in a form transmittable as image point data.

As a further component, the apparatus according to the invention has, as depicted in the FIGURE, an evaluation unit 6 that is connected to the image capture unit 4 and that captures the image point data provided by the image capture unit 4.

On the basis of the captured image point data, the evaluation unit 6 is capable, according to the invention, of ascertaining any active movement of the animal for slaughter 1. To this end, by way of example, a first step involves the image capture unit 4 capturing image points in the relevant section of the surface of the animal for slaughter 1 prior to delivery of the stimulation stimulus 3, and the relevant image point data being captured as reference image point data by the evaluation unit 6. A second step then involves delivery of the stimulation stimulus 3 to the animal for slaughter 1 and fresh capture of the image points in the relevant section of the surface of the animal for slaughter 1 being effected. The relevant image point data are subsequently captured by the evaluation unit 6 as comparison image point data and compared with the reference image point data. In the case of an active movement, a changes in the positional relationships of the image points would arise.

If the evaluation unit 6 establishes during the image point data comparison that changes in the positional relationships of the image points arose and the changes exceeds a previously defined limit value, then the animal for slaughter 1 has performed an active movement as a reaction to the stimulation stimulus 3. In this case, the stunning of the animal for slaughter 1 is classified as not right by the evaluation unit 6, and a corresponding check result, for example as a red visual signal, is output. The animal for slaughter 1 is accordingly transferred, manually or automatically, out of the regular process of processing animals for slaughter and is routed to a restunning section. After the restunning has been performed, another stun check is performed by the apparatus according to the invention in the present case.

If, by contrast, the result of the comparison of the comparison image point data with the reference image point data does not reveal sufficient changes in the positional relationships of the image points, then the animal for slaughter 1 has not performed an active movement as a reaction to the stimulation stimulus 3. In this case, the stunning of the animal for slaughter 1 is classified as in order by the evaluation unit 6 and a corresponding check result, for example as a green visual signal, is output. The animal for slaughter 1 is accordingly routed to exsanguination, in accordance with the regular process of processing animals for slaughter.

For the purpose of outputting the visual signal, the evaluation unit 6 in the present exemplary embodiment has an associated display unit 7.

In a further embodiment of the invention, the check result provided by the evaluation unit is used to actuate external units (not depicted). In the present case, external units of this kind are particularly sorting units that, in the event of inadequate stunning, fully automatically transfer the animal for slaughter 1 out of the process of processing animals for slaughter and route it to restunning.

In this embodiment of the invention, the check result is additionally output by the evaluation unit 6 as a control signal that is in turn capturable and processable by the external units.

The individual steps of stimulation stimulus delivery, image capture, movement ascertainment and check result output that are performable by the apparatus according to the invention take place in real time in the exemplary embodiment, which means that firstly the ongoing process of processing animals for slaughter is not unnecessarily disrupted and secondly inadequate stunning of the animal for slaughter 1 is detected as quickly as possible and appropriate restunning can be performed.

REFERENCE SYMBOLS USED

1 Animal for slaughter
2 Stimulation unit
3 Stimulation stimulus
4 Image capture unit
5 Image capture region
6 Evaluation unit
7 Display unit

The invention claimed is:

1. An apparatus for checking the stunning of an animal for slaughter, comprising:
   a stimulation unit for delivering a stimulation stimulus to the animal for slaughter;
   an image capture unit having an image capture region, said image capture unit being a 3D camera, said image capture unit optically capturing a section of a surface of the animal for slaughter in the image capture region and capturing image points in the section of the surface, the image points being provided as transmittable image point data; and
   an evaluation unit connected to the image capture unit and capturing the image point data provided by the image capture unit, said evaluation unit ascertaining an active movement of the animal for slaughter from the captured image point data and in the event of an ascertained active movement of the animal for slaughter, said evaluation unit providing a check result in a form capable of being output.

2. The apparatus as claimed in claim 1, wherein said 3D camera is a time-of-flight camera.

3. The apparatus as claimed in claim 1, wherein said stimulation unit is configured to deliver a contactless stimulation stimulus.

4. The apparatus as claimed in claim 3, wherein said stimulation unit is configured to deliver a thermal stimulation stimulus.

5. The apparatus as claimed in claim 4, wherein the thermal stimulation stimulus is a jet of steam.

6. The apparatus as claimed in claim 1, wherein the provided check result controls external units.

7. The apparatus as claimed in claim 1, wherein the provided check result is associated with a data record relating to the animal for slaughter.

* * * * *